(12) United States Patent
Pavaskar et al.

(10) Patent No.: US 9,399,003 B2
(45) Date of Patent: Jul. 26, 2016

(54) BROAD SPECTRUM ROOT CANAL FILING COMPOSITION FOR ENDODONTRIC USAGE

(71) Applicant: Rajdeep S. Pavaskar, Bardez, Goa (IN)

(72) Inventors: Rajdeep S. Pavaskar, Bardez (IN); Ida de Noronha de Ataide, Alto Porvorim (IN); Paul Chalakkal, Chicalim (IN); Nathan de Noronha de Ataide, Alto Porvorim (IN); Kristlee Sabrin Fernandes, Salcette (IN); Rahul Wagle, Margoa (IN); Ramchandra Keny, Panaji (IN); Devika Dhond, Bardez (IN); Maria Jose Wiseman Pinto, Talegoa (IN); Padmanabh V. Rataboli, Post Betim (IN); Anagha J. Kamath, Karnataka (IN)

(73) Assignee: Rajdeep S. Pavaskar, Bardez, Goa (IN)

( * ) Notice: Subject to any disclaimer, the term of this patent is extended or adjusted under 35 U.S.C. 154(b) by 98 days.

(21) Appl. No.: 14/345,161

(22) PCT Filed: Sep. 17, 2012

(86) PCT No.: PCT/IN2012/000619
§ 371 (c)(1),
(2) Date: Mar. 14, 2014

(87) PCT Pub. No.: WO2013/072922
PCT Pub. Date: May 23, 2013

(65) Prior Publication Data
US 2014/0234442 A1    Aug. 21, 2014

(30) Foreign Application Priority Data
Sep. 15, 2011 (IN) .......................... 2619/MUM/2011

(51) Int. Cl.
*A61K 6/00* (2006.01)
*A61K 31/422* (2006.01)

(52) U.S. Cl.
CPC ............. *A61K 6/0035* (2013.01); *A61K 6/0067* (2013.01)

(58) Field of Classification Search
CPC . A61K 6/0035; A61K 6/0032; A61K 6/0067; A61K 31/422
See application file for complete search history.

(56) References Cited

U.S. PATENT DOCUMENTS

| 5,116,603 | A | * | 5/1992 | Friedman | A61K 9/0063 424/49 |
| 5,139,768 | A | * | 8/1992 | Friedman | A61K 6/0017 424/45 |
| 6,124,374 | A | * | 9/2000 | Kolias | A61K 6/0026 106/35 |
| 2009/0285766 | A1 | * | 11/2009 | Kishen | A61K 8/34 424/49 |

FOREIGN PATENT DOCUMENTS

| AU | WO 2013013275 A1 | * | 1/2013 | ........... A61K 6/0067 |
| FI | WO 0053150 A1 | * | 9/2000 | ........... A61K 6/0035 |
| FR | EP 0408455 A1 | * | 1/1991 | ........... A61K 6/0035 |

OTHER PUBLICATIONS

Sun, Jinglu, et al. "Occurrence, population structure, and antimicrobial resistance of enterococci in marginal and apical periodontitis." Journal of clinical microbiology 47.7 (2009): 2218-2225.*

Fava, L. R. G., and W. P. Saunders. "Calcium hydroxide pastes: classification and clinical indications." International endodontic journal 32.4 (1999): 257-282.*

* cited by examiner

*Primary Examiner* — Bethany Barham
*Assistant Examiner* — Peter Anthopolos
(74) *Attorney, Agent, or Firm* — Blank Rome LLP

(57) ABSTRACT

Disclosed is dental root canal filling (intracanal medicament) compositions that are effective against resistant root canal infections caused by *Enterococcus faecalis* and Vancomycin-resistant Enterococci.

4 Claims, No Drawings

BROAD SPECTRUM ROOT CANAL FILING COMPOSITION FOR ENDODONTRIC USAGE

This application is the U.S. national phase of International Patent Application No. PCT/IN2012/000619, filed Sep. 17, 2012, which claims the benefit of Indian Patent Application No. 2619/MUM/2011, filed Sep. 15, 2011.

FIELD OF THE INVENTION

The present invention relates, in general, to the field of endodontic materials suitable for root canal filling and, in particular, to a dental root canal filling composition that are effective against most infection causing root canal based micro organisms including resistant root canal infections caused by *Enterococcus faecalis* and Vancomycin-resistant Enterococci.

BACKGROUND OF THE INVENTION

*Enterococcus faecalis* has often been isolated from asymptomatic and persistant root canal infections, chronic apical periodontitis and failed endodontic cases. It can survive in dentinal tubules for up to 10 days without nutrient supply. Serine protease and Ace aid in the adhesion of *Enterococcus faecalis* with dentin.

Calcium hydroxide has widely been accepted and used as a dental intracanal medicament because of its antimicrobial properties and its action on gram negative bacteria. It releases hydroxyl ions that are responsible for the creation of high alkalinity which has a destructive effect on bacterial cytoplasmic membrane and protein structure. The cytoplasmic membrane in most organisms is similar, irrespective of morphologic, tinctorial and respiratory characteristics of the organism. This means that calcium hydroxide will have similar effects on aerobic, anaerobic, gram positive and gram negative organisms. A pH of 10.5-11 delays the growth of *Enterococcus faecalis*, while a pH of 11 or more is known to eliminate *Enterococcus faecalis*. However, *Enterococcus faecalis* contains a proton pump that carries protons to the interior of the cell, acidifying its cytoplasm in situations of increased alkalinity in its environment. Thus, *Enterococcus faecalis* has been found to be resistant to most intracanal medicaments containing calcium hydroxide.

Linezolid is a synthetic antibiotic of the oxazolidinone group. It has been shown to be effective only on gram positive organisms. It inhibits protein synthesis in micro-organisms by disrupting the translation of messenger RNA (mRNA) into proteins in the ribosome. Linezolid acts during the initiation of protein synthesis by binding to the 23S portion of the 50S subunit (the centre of peptidyl transferase activity), preventing the formation of 70S ribosome complex that is responsible for the formation of the 'initiation complex' (composed of 30S and 50S subunits of the ribosomes, tRNA and mRNA).

Linezolid has been medically used for the treatment of skin and soft tissue infections, diabetic foot infections, pneumonia, infective endocarditis, tuberculosis, neutropenia, endophthalmos, meningitis, bone and joint infections including chronic osteomylitis. It has also shown to be effective against certain organisms which are also found inside root canals of teeth like: *Staphylococccus aureus, Streptococcus agalactiae, Streptococcus pneumonia, Streptococcus pyogens, Streptococcus viridans* group, *Listeria monocytogenes* and *Corynebacterium*. Linezolid is also effective against organisms responsible for resistant root canal infections like *Enterococcus faecalis*, Vancomycin-resistant *Enterococcus faecalis* and Vancomycin-resistant Enterococci.

The present inventors have meticulously carried out earnest work and devised a dental root canal filling composition that is very effective resistant root canal infections caused by *Enterococcus faecalis* and Vancomycin-resistant Enterococci.

SUMMARY OF THE INVENTION

The present invention is directed to provide dental root canal filling compositions for use during an endodontic procedure. The dental root canal filling compositions according to the present invention comprises an antibiotic agent linezolid, calcium hydroxide and other pharmaceutically acceptable excipients.

The dental root canal filling compositions according to the present invention are effective against resistant root canal infections caused by *Enterococcus faecalis* and Vancomycin-resistant Enterococci.

These and other additional features of the present invention will become more fully apparent from the following description and appended claims, or may be learned by the practice of the invention as set forth hereinafter.

DETAILED DESCRIPTION OF THE INVENTION

The present invention will be described with respect to particular embodiments but the invention is not limited thereto only by the claims. Where an indefinite or definite article is used when referring to a singular noun e.g. "a" or "an", "the", this includes a plural of that noun unless something else is specifically stated.

In the embodiments of the present invention, the dental root canal filling composition comprises of 2 to 10% by weight of linezolid, 30 to 60% by weight of calcium hydroxide, 2 to 20% by weight of a tackifier selected from the group consisting of polyethylene glycol, polyvinyl pyrrolidone, polyvinyl methylether, carbopol or a combination thereof, and 30 to 65% by weight of liquid paraffin.

In some embodiments of the present invention, the dental root canal composition further comprises a radio-opaque material selected from but not limited to barium sulphate, bismuth subnitrate, bismuth trioxide, bismuth carbonate and zirconium oxide. In some preferred embodiments, amount of the radio-opaque material is preferably 5 to 20 parts by weight based on 100 parts by weight of the filling composition.

In some embodiments of the present invention, the dental root canal composition further comprises a disinfectant in amount of 0.5 to 5 parts by weight based on 100 parts by weight of the filling composition. In some preferred embodiments, the disinfectant is selected from iodoform and iodine.

The following examples illustrate the present invention and are not to be construed as limiting the spirit and scope of the invention.

EXAMPLE 1

A dental root canal filling composition was formed having the following components and concentrations range: 2-10% by weight of linezolid, 30-60% by weight of calcium hydroxide, 2-20% by weight of polyethylene glycol, 5-20 parts by weight of barium sulphate based on 100 parts by weight of the filling composition, 0.5-5 parts by weight of iodoform based on 100 parts by weight of the filling composition, and 30-65% by weight of liquid paraffin.

EXAMPLE 2

A dental root canal filling composition was formed having the following components and concentrations range: 2-10% by weight of linezolid, 30-60% by weight of calcium hydroxide, 2-20% by weight of polyethylene glycol, 5-20 parts by weight of barium sulphate based on 100 parts by weight of the filling composition, 0.5-5 parts by weight of iodine based on 100 parts by weight of the filling composition, and 30-65% by weight of liquid paraffin.

EXAMPLE 3

A dental root canal filling composition was formed having same components and concentrations as in Examples 1-2 except that polyvinyl pyrrolidone was used instead of polyethylene glycol.

EXAMPLE 4

A dental root canal filling composition was formed having same components and concentrations as in Examples 1-2 except that polyvinyl methylether was used instead of polyethylene glycol.

EXAMPLE 5

A dental root canal filling composition was formed having same components and concentrations as in Examples 1-2 except that carbopol was used instead of polyethylene glycol.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

The invention claimed is:

1. A dental root canal filling composition comprising 2 to 10% by weight of linezolid, 30 to 60% by weight of calcium hydroxide, 2 to 20% by weight of tackifier selected from the group consisting of polyethylene glycol, polyvinyl pyrrolidone, polyvinyl methylether and carbopol, and 30 to 65% by weight of liquid paraffin.

2. The dental root canal filling composition as claimed in claim 1 further comprising 5 to 20 parts by weight of a radio-opaque material based on 100 parts of the filling composition.

3. The dental root canal filling composition as claimed in claim 2 further comprising 0.5 to 5 parts by weight of a disinfectant selected from iodine and iodoform based on 100 parts of the filling composition.

4. The dental root canal filling composition as claimed in claim 2, wherein the radio-opaque material is selected from the group comprising of barium sulphate, bismuth subnitrate, bismuth trioxide, bismuth carbonate and zirconium oxide.

* * * * *